(12) United States Patent
Shikami et al.

(10) Patent No.: US 7,260,244 B2
(45) Date of Patent: Aug. 21, 2007

(54) PRINT INSPECTION METHOD AND PRINT INSPECTION APPARATUS

(75) Inventors: Masaki Shikami, Ibaraki (JP); Hirofumi Torita, Ibaraki (JP)

(73) Assignee: Nitto Denko Corporation, Osaka (JP)

( * ) Notice: Subject to any disclaimer, the term of this patent is extended or adjusted under 35 U.S.C. 154(b) by 930 days.

(21) Appl. No.: 10/667,075

(22) Filed: Sep. 18, 2003

(65) Prior Publication Data
US 2004/0057629 A1    Mar. 25, 2004

(30) Foreign Application Priority Data
Sep. 20, 2002    (JP)    ............... 2002-275115

(51) Int. Cl.
G06K 9/00    (2006.01)
G06K 9/42    (2006.01)
G06K 9/64    (2006.01)

(52) U.S. Cl. ............... 382/112; 382/141; 382/217; 382/257; 348/86; 348/125; 356/237.1

(58) Field of Classification Search ............... 382/112, 382/141–152, 217–223, 257; 348/86–95, 348/125–134; 356/237.1–237.6
See application file for complete search history.

(56) References Cited

U.S. PATENT DOCUMENTS

| | | | | |
|---|---|---|---|---|
| 5,365,596 A | * | 11/1994 | Dante et al. | 382/141 |
| 5,828,771 A | * | 10/1998 | Bloomberg | 382/112 |
| 5,848,189 A | * | 12/1998 | Pearson et al. | 382/218 |
| 6,061,476 A |  | 5/2000 | Nichani |  |
| 6,269,194 B1 | * | 7/2001 | Nichani | 382/270 |
| 7,017,492 B2 | * | 3/2006 | Seymour | 101/484 |
| 2005/0074140 A1 | * | 4/2005 | Grasso et al. | 382/103 |

FOREIGN PATENT DOCUMENTS

| | | |
|---|---|---|
| EP | 06343293 | 3/1995 |
| EP | 0703698 | 3/1996 |
| JP | 02163879 | 6/1990 |
| JP | 06201611 | 7/1994 |
| JP | 0792103 | 4/1995 |
| JP | 07-186375 | 7/1995 |
| JP | 08207258 | 8/1996 |

\* cited by examiner

*Primary Examiner*—Bhavesh M Mehta
*Assistant Examiner*—Aaron W Carter
(74) *Attorney, Agent, or Firm*—Berliner & Associates

(57) ABSTRACT

A method of inspecting a defect on a surface of a printed matter includes a step of applying a gray scale erosion filter to a non-defect surface of a printed matter to prepare a gray scale erosion filter applied image and then adding a predetermined density value to the gray scale erosion filter applied image, thereby preparing a reference image, a step of subtracting a captured image of the surface of the printed matter to be inspected from the reference image, thereby preparing a differential image, and a step of applying a density compensation process to the differential image to prepare a density compensated image, then applying an edge detection filter to the density compensated image to prepare an edge detection filter applied image and then converting the edge detection filter applied image into binary data according to a predetermined threshold value.

10 Claims, 10 Drawing Sheets

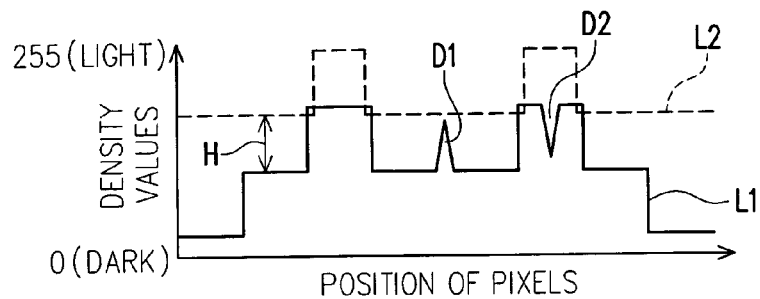
F I G . 6(a)
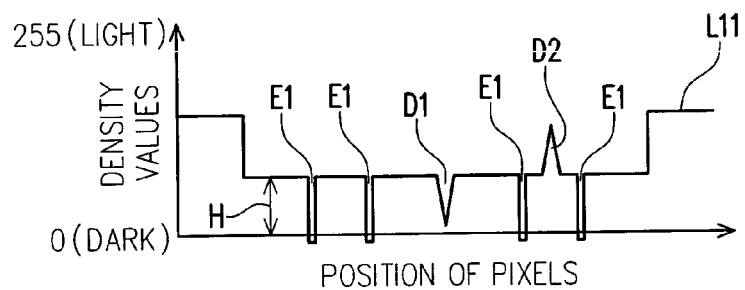
F I G . 6(b)
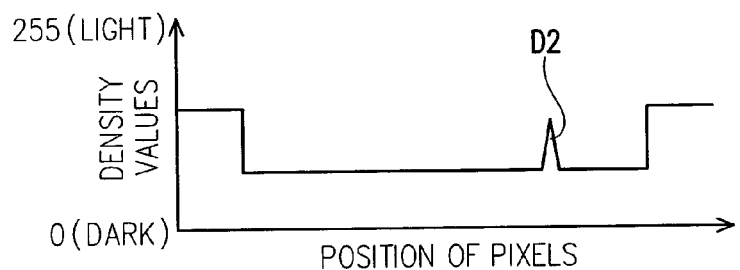
F I G . 6(c)
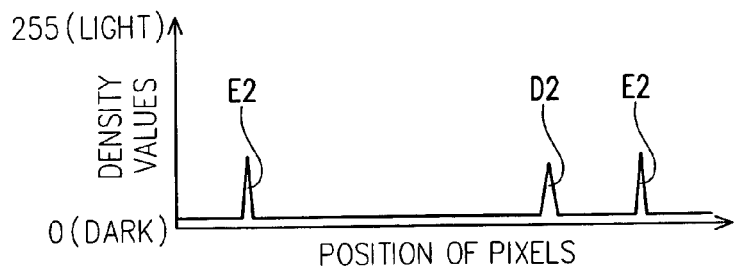
F I G . 6(d)

FIG.10(a)

| -1 | 0 | 1 |
|----|---|---|
| -2 | 0 | 2 |
| -1 | 0 | 1 |

FIG.10(b)

| 1  | 2  | 1  |
|----|----|----|
| 0  | 0  | 0  |
| -1 | -2 | -1 |

PRINT INSPECTION METHOD AND PRINT INSPECTION APPARATUS

CROSS REFERENCE TO RELATED APPLICATION

This application claims priority from Japanese Patent Application No. 2002-275115, which is incorporated herein by reference.

BACKGROUND OF THE INVENTION

1. Field of the Invention

The present invention relates to an inspection method and apparatus that are capable of detecting defects such as stains or spots on the surface of a printed matter, printed character deficiencies and the like, and more particularly to an inspection method and apparatus that is capable of detecting these defects of printed matters with high accuracy by reducing influences of positional displacement of a printed matter, warped printed matter and any other printed matters conveyed under various conditions on a conveyor line or other conveyor means particularly during they are conveyed independently of each other in a sequential order. The aforesaid defects also represent any foreign matters such as dusts mixed into the inside of a printed matter, which are visible through the surface of the printed matter when the printed matter is made of a transparent and/or opaque material with printed information thereon (e.g., a paper packet for a dose of medicine).

2. Discussion of the Background

A known method to determine the presence of a defect of a printed matter involves capturing as an inspection object an image of such as a continuously-conveyed elongated printed matter to produce an inspection image (a captured image of the surface of the printed matter), and comparing the inspection image to a reference image (a captured image of the surface of a non-defect printed matter) on a pixel-by-pixel basis, so that a defect is recognized as "present" at a pixel where the density difference is larger than a predetermined value.

In the above prior method, where positional displacement exists between the compared reference image and inspection image, accurate detection of the defect is unlikely to be made. In order to address this problem, various methods for accurate positioning both images were proposed.

Another approach to address the above problem hitherto proposed is to reduce the possibility of misjudgment due to error in image positioning by masking a specific region of a printed matter such as an edge of a printed image at which a sharp increase or decease in density difference occurs if the positional displacement has been caused, so that such a region is removed from the inspection image.

Still another approach to address the above problem hitherto proposed such as in Japanese Patent Application Laid-open No. Hei-7-186375 is to detect a defect while avoiding the occurrence of a region, which might be removed from the inspection image by the masking process, by applying a gray scale dilation filter or a gray scale erosion filter to any one of the reference and inspection images, generating a differential image and converting the same into binary data.

However, the inspection methods as described above each are intended to inspect printed matters successively conveyed under a secured condition. Therefore, these methods may not accurately inspect printed matters conveyed under unstabilized imaging condition (e.g., lighting condition), such as those conveyed independently of each other in a sequential order under various conditions, which are likely to be relatively largely displaced from the correct or intended position within the imaging field of view, or warped. Hence, the conventional methods have a problem that a minor defect of such printed matters may not be detected only by converting a differential image into binary data.

Particularly, where printed matters to be inspected are provided by punching or die cutting a substrate on which printing has been applied, punching errors must be taken into account. That is, such punching error makes it unlikely to punch or die cut the matter at a constant position in every operation, with the result that printed matters produced by punching or die cutting may have different contours and cause positional displacement on the conveyor. Thus, the positional displacement of the contour of the inspection image relative to the contour of the reference image already exists before the inspection, thus posing a problem of necessarily causing a region, which may not be inspected on the basis of the differential image.

The present invention has been conceived to address the above problems. It is an object of the present invention to provide an inspection method and apparatus that are capable of achieving inspection of a defect with high accuracy by reducing influences of printed matters, which have been displaced from the correct or intended position during the conveyance, or warped printed matters.

It is another object of the present invention to provide an inspection method and apparatus that are capable of achieving inspection of a defect with high accuracy by reducing influences of printed matters, which have contours displaced from each other, such as those produced by punching or die cutting a substrate with printing applied thereon.

SUMMARY OF THE INVENTION

To achieve the above objects, there is provided a method of inspecting a defect on a surface of a printed matter, which includes: a step of applying a gray scale erosion filter to a non-defect surface of a printed matter to prepare a gray scale erosion filter applied image and then adding a predetermined density value to the gray scale erosion filter applied image, thereby preparing a reference image; a step of subtracting a captured image of the surface of the printed matter to be inspected from the reference image, thereby preparing a differential image; and a step of applying a density compensation process to the differential image to prepare a density compensated image, then applying an edge detection filter to the density compensated image to prepare an edge detection filter applied image and then converting the edge detection filter applied image into binary data according to a predetermined threshold value.

According to the above method, the gray scale erosion filter is applied to the non-defect surface of a printed matter and adding a predetermined density value to the gray scale erosion filter applied image. Herein, by the gray scale erosion filter is meant a process that designates a minimum density value in a peripheral region (e.g., a 3 by 3 pixel region and a 5 by 5 pixel region) of a target pixel as a new density value of the target pixel. This application of the gray scale erosion filter allows a dark region (a region having a lower density value) of the captured image to have a large size, while a light region (a region having a higher density value) to have a small size, thus enabling the acceptance of the positional displacement by an amount corresponding to this changing. Then, a predetermined density value is added to the gray scale erosion filter applied image so that the reference image has in its entire region a high density value except for an edge region where change in size has been caused. Thus, it is possible to reduce the influence of a printed matter having uneven density due to its positional displacement or warping to a differential image.

Then, a captured image of the surface of the printed matter to be inspected is subtracted from the reference image, thereby preparing a differential image. Accordingly, a defect darker than the non-defect surface (hereinafter referred to a dark defect) of the thus prepared differential image has a positive property (a property enabling a density value higher than peripheral pixels), while a defect lighter than the non-defect surface (hereinafter referred to a light defect) has a negative property (a property enabling a density value lower than peripheral pixels).

Then, the density compensation process (a process to compensate a region having a negative property with the density value of a peripheral region) is applied to the differential image, so that only a region having the positive property (dark defect) becomes prominent. Then, the edge detection filter such as a Sobel filter is applied to the density compensated image. Thus, it is possible to reduce the influence of a printed matter having uneven density (shading) due to its positional displacement or warping, and hence achieve the conversion process into binary data under a secured condition.

With the above described method, it is possible to detect defects of the printed matters with high accuracy by reducing influences of positional displacement of a printed matter during the conveyance, warped printed matter and any other printed matters conveyed under various conditions. By the defects on a surface of a printed matter is meant not only stains or spots, printed character deficiencies and any other defects actually caused on the surface of the printed matter, but also any foreign matters such as dusts mixed into the inside of a printed matter, which are visible through the surface of the printed matter when the printed matter is made of a transparent and/or opaque material with printed information thereon (e.g., a paper packet for a dose of medicine).

Likewise, in order to detect a light defect, there is provided a method of inspecting a defect on a surface of a printed matter, which comprises: a step of applying a gray scale dilation filter to a captured image of a non-defect surface of a printed matter to prepare a gray scale dilation filter applied image and then subtracting a predetermined density value from the gray scale dilation filter applied image, thereby preparing a reference image; a step of subtracting the reference image from a captured image of the surface of the printed matter to be inspected, thereby preparing a differential image; and a step of applying a density compensation process to the differential image to prepare a density compensated image, then applying an edge detection filter to the density compensated image to prepare an edge detection filter applied image and then converting the edge detection filter applied image into binary data according to a predetermined threshold value. Herein, by the gray scale dilation filter is meant a process that designates a maximum density value in a peripheral region (e.g., a 3 by 3 pixel region and a 5 by 5 pixel region) of a target pixel as a new density value of the target pixel.

Preferably, the density compensation process is achieved by applying a gray scale dilation filter and a gray scale erosion filter, respectively. This application of the gray scale dilation filter compensates the density of a region having a negative property, which causes a defect having a positive property to have a large size. The gray scale erosion filter is applied so as to return the size of the enlarged defect to an original size.

Alternatively, the density compensation process may be achieved by applying a density conversion process. As this density conversion process, a density conversion process, which involves converting a region having a density value lower than the added (subtracted) density value into the added (subtracted) density value, while keeping a region having a density higher than the added (subtracted) density value intact, is applicable.

In order to achieve inspection of a defect with high accuracy by reducing influences of printed matters, which have contours displaced from each other, such as those produced by punching or die cutting a substrate with printing applied thereon, the reference image is prepared on the basis of a captured image of a non-defect surface of the matter in a state prior to be punched or die cut.

According to the above method, the reference image is prepared on the basis of the captured image of a non-defect surface of the matter in a state prior to be punched or die cut, so that even if the contour of the printed matter to be inspected is itself displaced, it can be compared with the reference image. As a result, it is possible to detect a defect with high accuracy.

In order to achieve inspection of a defect with high accuracy by reducing influences of printed matters, which have been displaced from the correct or intended position during the conveyance, or warped printed matters, there is also provided an apparatus for inspecting a defect on a surface of a printed matter including: an imaging device for capturing a surface of a printed matter to prepare a captured image; and an image processing device for applying image processing to the captured image of the surface of the printed matter; wherein the image processing device includes: a means of applying a gray scale erosion filter to a captured image of a non-defect surface of a printed matter to prepare a gray scale erosion filter applied image; a means of preparing a reference image by adding a predetermined density value to the gray scale erosion filter applied image; a means of preparing a differential image by subtracting a captured image of a surface of a printed matter to be inspected from the reference image; a means of applying a density compensation process to the differential image to prepare a density compensated image; a means of applying an edge detection filter to the density compensated image to prepare an edge detection filter applied image; and a means of converting the edge detection filter applied image into binary data according to a predetermined threshold value.

According to still another aspect of the present invention, there is provided an apparatus for inspecting a defect on a surface of a printed matter comprising: an imaging device for capturing a surface of a printed matter to prepare a captured image; and an image processing device for applying image processing to the captured image of the surface of the printed matter; wherein the image processing device includes: a means of applying a gray scale dilation filter to a captured image of a non-defect surface of a printed matter to prepare a gray scale dilation filter applied image; a means of preparing a reference image by subtracting a predetermined density value from the gray scale dilation filter applied image; a means of preparing a differential image by subtracting the reference image from a captured image of a surface of a printed matter to be inspected; a means of applying a density compensation process to the differential image to prepare a density compensated image; a means of applying an edge detection filter to the density compensated image to prepare an edge detection filter applied image; and a means of converting the edge detection filter applied image into binary data according to a predetermined threshold value.

BRIEF DESCRIPTION OF THE DRAWINGS

The above, and other objects, features and advantages of the present invention will become apparent from the detailed description thereof in conjunction with the accompanying drawings wherein.

FIG. 6a-6d respectively illustrate explanatory views for stepwisely explaining an inspection process for dark defects in a non-warped printed matter.

FIG. 9a-8d respectively illustrate explanatory views for stepwisely explaining an inspection operation for light defects in a warped printed matter.

FIGS. 10a and 10b respectively illustrate examples of a Sobel filter.

DETAILED DESCRIPTION OF THE PREFERRED EMBODIMENT

An embodiment according to the present invention will be hereinafter described with reference to the accompanying drawings.

Figure 1:
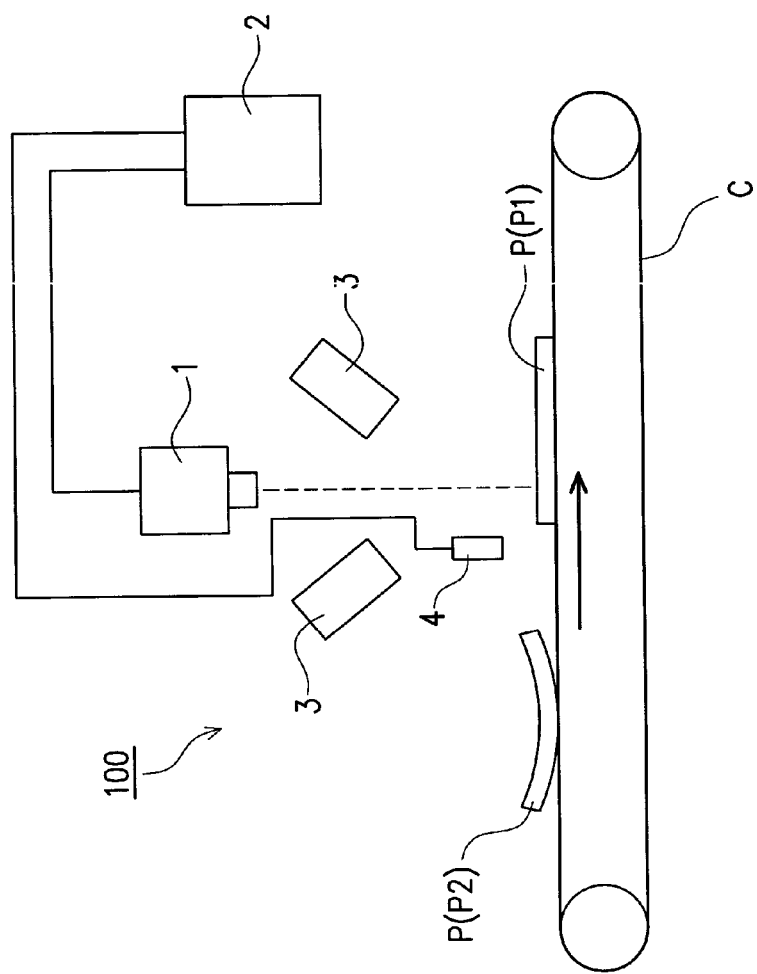
FIG. 1 is a schematic structural view of an inspection apparatus, which carries out the inspection method according to an embodiment of the present invention.

FIG. 1 is a schematic structural view of an inspection apparatus, which carries out the inspection method according one embodiment of the present invention. As illustrated in FIG. 1, an inspection apparatus 100 of this embodiment includes an area scan CCD camera 1 as an imaging device for capturing an image of the surface of each printed matter P transferred on a conveyor C, and an image processing device 2 for applying image processing to an image of the surface of each printed matter P captured by the CCD camera 1 so as to detect defects such as stains, spots or printed character deficiencies on the surface of the printed matter, as well as foreign matters intruded into the inside of a bag-shaped printed matter made of a transparent and/or opaque material.

The inspection apparatus 100 of this embodiment includes lighting devices 3 for illuminating the surface of each printed matter P from the side thereof and an optical sensor 4 for detecting each printed matter P passing thereunder, so that an image output from the CCD camera 1 is input into the image processing device 2 at a predetermined timing after the sensor 4 has detected each printed matter P passing thereunder.

Figure 2:
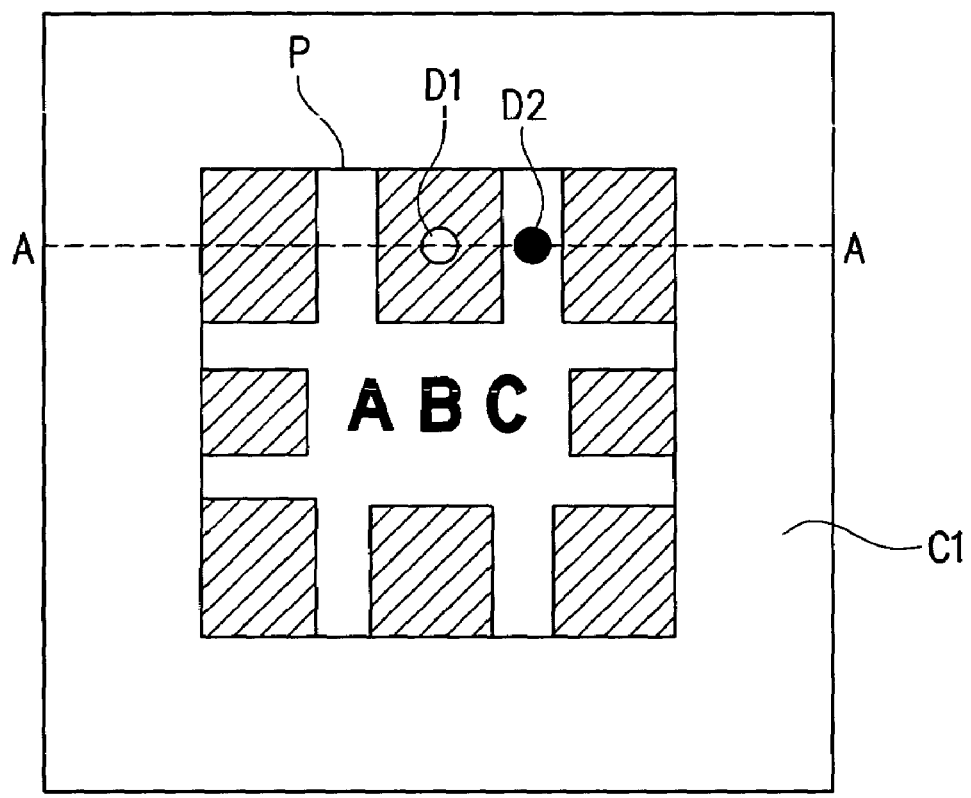
FIG. 2 illustrates an example of an image of a printed matter captured by an imaging device of FIG. 1.

FIG. 2 illustrates an example of an image of each printed matter P captured by the CCD camera 1. As illustrated in this Figure, the imaging field of view of the CCD camera 1 is set to be larger than the size of the printed matter P, thereby enabling secured capturing of the image of the entire surface of the printed matter P, which may be displaced from the correct or intended position during the conveyance. This results in capturing an image of an surface C1 of the conveyor 1 along with the image of the surface of the printed matter P. Accordingly, in order to securely extract the contour of each printed matter P, it is preferable to make the surface C1 of the conveyor C from a material enabling the surface C1 to have a large contrast to the surface of the printed matter P or to color the same, as described later. In FIG. 2, the reference codes D1 and D2 respectively represent a light defect and a dark defect.

Figure 3:
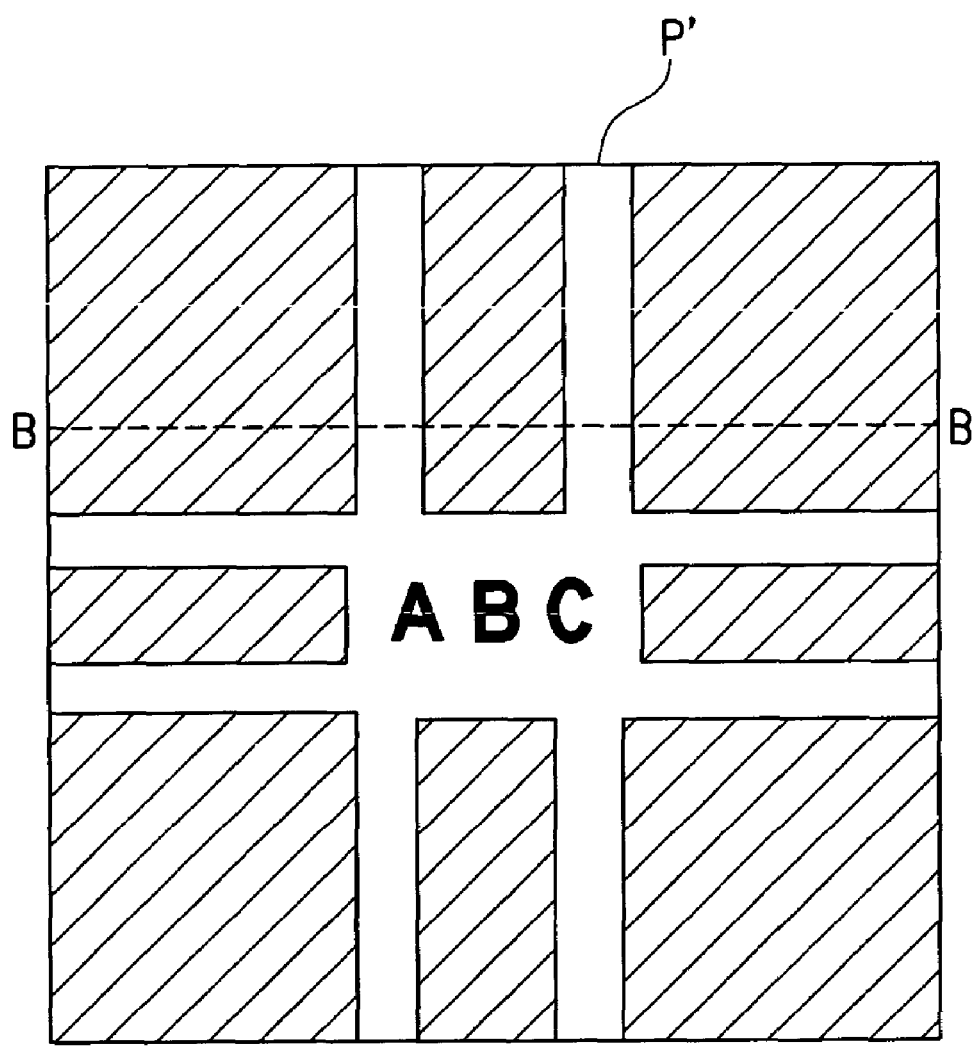
FIG. 3 illustrates an example of an image of a substrate captured by the imaging device of FIG. 1.

The printed matters P in this embodiment each are produced by punching or die cutting a substrate on which printing has been applied. FIG. 3 illustrates an example of an image of a substrate P' captured by the CCD camera 1. As can be seen by the comparison between FIGS. 2 and 3, the printed matter P is produced by punching out the center of the substrate P'. As described later, the inspection apparatus 100 of this embodiment employs the captured image of a non-defective surface of the substrate P' as a reference image, thus enabling highly accurate inspection with no influence of the printed matter P which has been displaced from the correct or intended position (or caused positioning error in punching).

The image processing device 2 is made up by utilizing a general purpose personal computer, which includes an A/D conversion board, an image memory, a control unit (not shown) made up of a CPU that controls their operations, as well as running a predetermined image processing program previously stored. Now, the description will be made specifically for the operation of the image processing program which is run in the image processing device 2, with reference to FIGS. 4-9. Herein, the operation is roughly categorized into a reference image preparation operation and an inspection-ongoing operation.

Reference Image Preparation Operation

Figure 4:
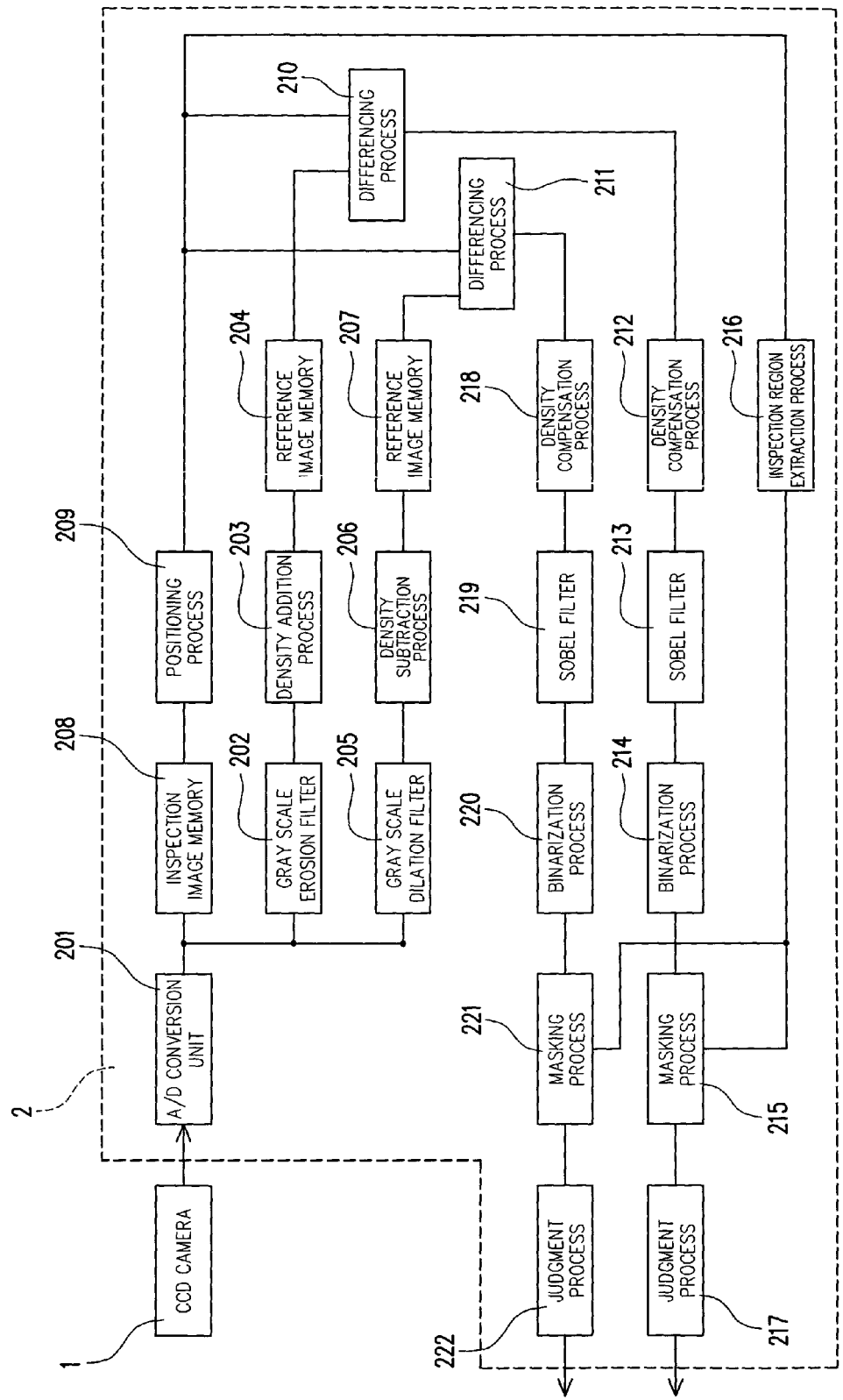
FIG. 4 illustrates a functional block diagram of an image processing device of FIG. 1.
Figure 5A:
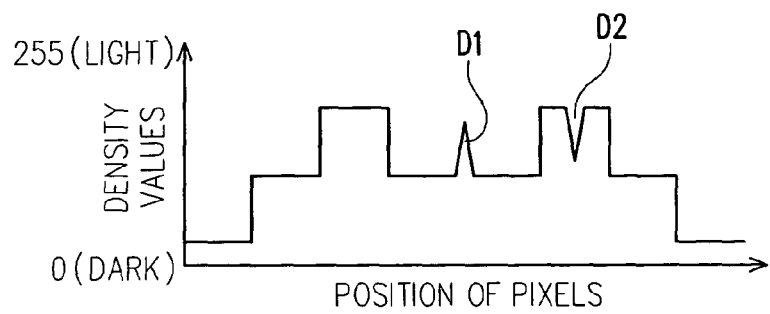
FIG. 5a-5a respectively illustrate density profiles of the images captured by the imaging device of FIG. 1.
Figure 5B:
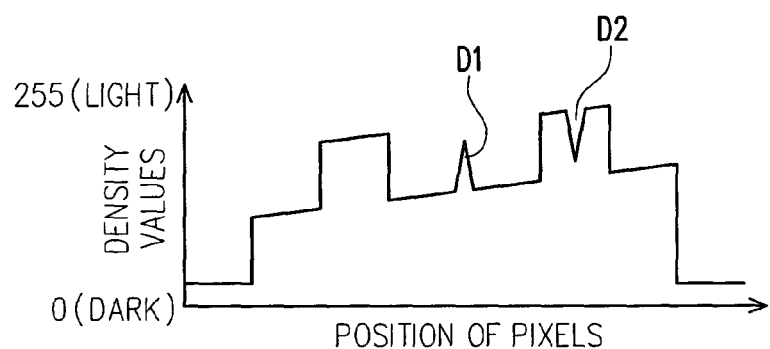
Figure 5C:
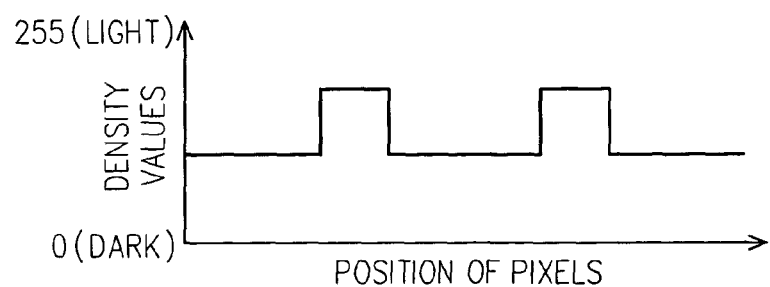

FIG. 4 illustrates a functional block diagram of the image processing device 2 according to this embodiment. As illustrated in this Figure, in order to prepare the reference image, an image (FIG. 3) of the substrate P' captured by the CCD camera 1 is converted into digital signals at an A/D conversion unit 201. More specifically, the A/D conversion unit 201 performs an 8-bit A/D conversion so as to allocate the values of 0-255 (density values) to pixels, in order from a low density pixel to a high density pixel. FIG. 5C illustrates a density profile taken along the line B-B (FIG. 3) in the captured image of the substrate P' which has been thus A/D converted.

Then, as illustrated in FIG. 4, a gray scale erosion filter 202 is applied to the A/D converted image by the control unit. Herein, by the gray scale erosion filter is meant a process that designates a minimum density value in a peripheral region (e.g., a 3 by 3 pixel region and a 5 by 5 pixel region) of a target pixel as a new density value of the target pixel, in which the peripheral region can be properly set in the parameter setting according to each case. The number of times at which the gray scale erosion filter 202 is applied can also be set in the parameter setting.

Then, the image to which the gray scale erosion filter 202 has been applied is subjected to a density addition process 203 by the control unit. That is, in order to reduce the influence of the printed matter P as an inspection target having uneven density due to its warping or the like, to a differential image, which will be described later, a predetermined density value is added to each of the pixels forming the image. The density value to be added (hereinafter referred to an additional density value) can be properly set in the parameter setting, so that where the printed matter is likely to have a relatively high degree of density unevenness, a large density value is preferably set.

The reference value thus prepared is stored in a reference image memory 204 so as to be utilized in detecting dark defects such as stains or spots.

On the other hand, a gray scale dilation filter 205 is also applied by the control unit to the captured image, which has been A/D converted at the A/D conversion unit 201. Herein, by the gray scale dilation filter is meant a process that designates a maximum density value in a peripheral region (e.g., a 3 by 3 pixel region and a 5 by 5 pixel region) of a target pixel as a new density value of the target pixel. The peripheral region and the number of times at which the gray scale dilation filter 205 is applied can also be set in the parameter setting.

Then, the image to which the gray scale dilation filter 205 has been applied is subjected to a density subtraction process 206 by the control unit so that a predetermined density value is subtracted from each of the pixels forming the image. In the same manner as the density addition process 203, the density value to be subtracted can be properly set in the parameter setting according to each case, and a large density value is preferably set where the printed matter is likely to have a relatively high degree of density unevenness.

The thus prepared reference image is stored in a reference image memory 207 so as to be utilized in detecting light defects such as printed character deficiencies.

Inspection-Ongoing Operation

Also, in order to actually inspect each printed matter P transferred on the conveyor C, an image (FIG. 2) of the printed matter captured by the CCD camera 1 is first converted into digital signals at the A/D conversion unit 201 and stored in an inspection image memory 208. FIGS. 5(a) and 5(b) respectively illustrate density profiles taken along the line A-A (FIG. 2) in the inspection image of the printed matter P thus stored in the inspection image memory 208. Specifically, FIG. 5(a) illustrates a density profile of the printed matter P, which has a low degree of density unevenness due to a condition of the printed matter free from warping or the like, and FIG. 5(b) illustrates a density profile of the printed matter P, which has a high degree of density unevenness ("P2" in FIG. 1) due to its warping or the like.

Then, the inspection image stored in the inspection image memory 208 is subjected to a positioning process 209 by the control unit. That is, since the printed matter P transferred on the conveyor C is likely to cause a relatively large positional displacement within the imaging field of view of the CCD camera 1, the positioning process 209 is performed in order to correct such a positional displacement. A known method can be properly applied to achieve the positioning process 209. For example, a characteristic portion (e.g., a letter "B" in FIG. 3) of the reference image stored in the reference image memory 204 or 207 as described above is previously determined as a target. Then, a portion, which is identical to the characteristic portion, is extracted from the inspection image such as by subjecting a comparison and normalization process. Then, the inspection image is moved in parallel with the reference image so as to match the relative position of the extracted portion of the reference image to the relative position of the characteristic portion of the reference image. Accordingly, even if the positioning process 209 is performed, it is hard to perfectly match the inspection image and the reference image to each other due to deformation of an image caused in a warped printed matter or positioning error. Therefore, as described above, an image to which the gray scale erosion filter 202 (or gray scale dilation filter 205) is applied is designated as a reference image, thereby making a subtle positional displacement of the image acceptable.

Then, the inspection image, to which the positioning process 209 has been applied, is subjected to a differencing process 210 by the control unit relative to the reference image stored in the reference image memory 204 in order to detect dark defects. Also, the inspection image, to which the positioning process 209 has been applied, is subjected to a differencing process 211 by the control unit relative to the reference image stored in the reference image memory 207 in order to detect light defects. The descriptions will be hereinafter made specifically for the process for the detection of dark defects and the process for the detection of light defects, respectively.

(1) Operation for Detection of Dark Defects

First of all, the description will be made for the operation for the detection of dark defects. FIG. 6 respectively illustrate explanatory views for stepwisely explaining an inspection operation for dark defects in the printed matter P having a low degree of density unevenness. The solid line L1 in FIG. 6(a) represents a density profile taken along the line A-A of the inspection image in FIG. 2, while the broken line L2 represents a density profile of the reference image taken along the line B-B (FIG. 3) stored in the reference image memory 204. That is, the broke line L2 represents a density profile after the captured image having a density profile illustrated in FIG. 5(c) is applied with the gray scale erosion filter 202 and then subjected to the density addition process 203 ("H" represents an additional density value).

In the differencing process 210, a differential image is prepared by subtracting the inspection image subjected to the positioning process 209 from the reference image stored in the reference image memory 204. By subjecting the differencing process 210, or subtracting the solid line L1 from the broken line L2 in FIG. 6(a), a differential image having a density profile as illustrated in FIG. 6(b) is prepared. In FIG. 6(b), some pixels are illustrated as being negative. In this regard, where the density values fall within the range of 0-255, they are clipped at 0 in the actual processing. However, it is a matter of course that negative values can be treated as density values by increasing the number of bits in A/D conversion at the A/D conversion unit 201, or allocating the density values in the range of −125 to 125 without increase of the number of bits.

Then, as illustrated in FIG. 4, the differential image prepared by the differencing process 210 is subjected to a density compensation process 212 by the control unit. Herein, by the density compensation process 212 is meant a process that fills a region having a negative property (a region having a lower density than the density of peripheral pixels) with the density value of the peripheral pixels. In this embodiment, the density compensation process 212 is achieved by applying the gray scale dilation filter and the gray scale erosion filter. More specifically, the gray scale dilation filter is repeatedly applied until a region having such a negative property is eliminated. This repeated application of the gray scale dilation filter causes the enlargement of the size of a defect having a positive property. In order to return it to a size approximate to the original size, the gray scale erosion filter is applied by the number of times equal or nearly equal to the number of times the gray scale dilation filter is applied. The number of times the gray scale dilation filter is to be applied in the density compensation process 212 depends on the width of an edge ("E1" in FIG. 6(b)) that depends on the number of times the aforesaid gray scale erosion filter 202 has been applied, accuracy of the density compensation process 212 or the like, and therefore the number of times, which has been previously and experimentally determined, is applied to compensate the density difference until at least the edge E1 having a negative property is eliminated. FIG. 6(c) illustrates a density profile of an image to which the aforesaid density compensation process 212 has been applied. This Figure illustrates an example of density compensation, in which not only the edge E1 but also a light defect D1 are illustrated as regions having a negative property, which have been density compensated. In this regard, it is to be noted that the density of the light defect D1 may not be completely compensated, which depends on the size of the light defect D1. However, such incomplete compensation of the density of the light defect D1, which makes the light defect D1 possible to be detected by a binarization process 214, may not pose a problem in a case in which it is enough to only recognize the presence of a defect. However, when it is necessary to identify whether a defect is the light defect D1 or the dark defect D2, the light defect D1 must be density compensated. Accordingly, the number of times the gray scale erosion filter is applied in the density compensation process 212 is determined by taking into account the size of a possible light defect as well.

Figure 7:
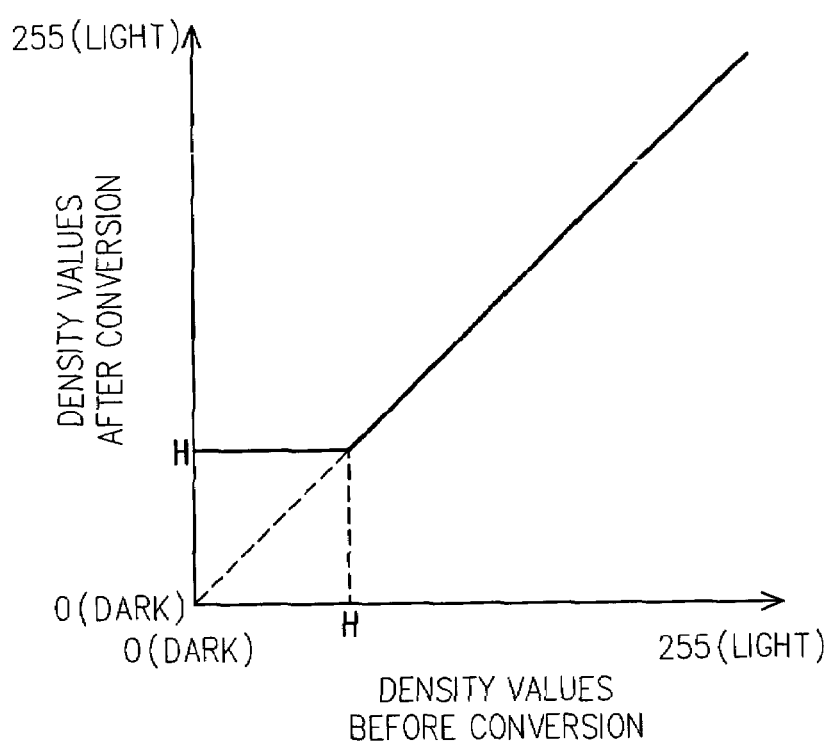
FIG. 7 is a graph illustrating an example of a density conversion process.

For the printed matter P having a low degree of density unevenness, as illustrated in FIG. 7, it is possible to achieve the density compensation process 212 by applying a density conversion process that converts all the density values lower than a predetermined value to a constant density value. A conversion curve illustrated in FIG. 7 represents an example where all the density values less than the additional density value H are converted to the additional density value H, and therefore is not intended to limit the present invention to this example. It is possible to apply a conversion curve with, for example, all the density values less than the additional density value H converted to 0.

Figures 10A, 10B:
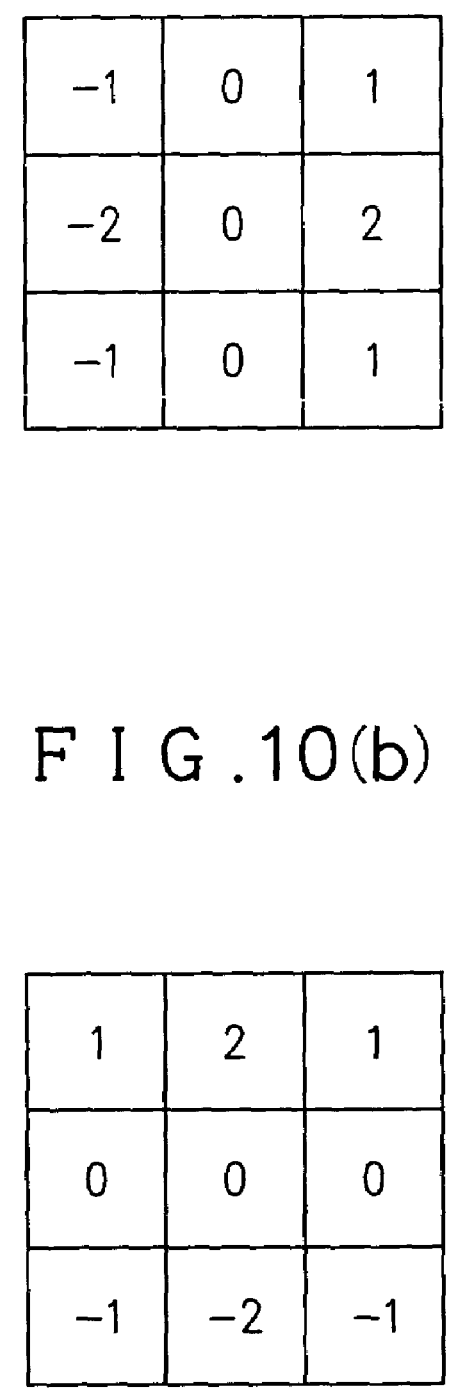

Then, as illustrated in FIG. 4, the image, to which the density compensation process 212 has been applied, is subjected to a Sobel filter 213 as an edge detection filter by the control unit. Herein, the Sobel filter 213 involves creating a 3 by 3 pixel operator (FIG. 10(a)) for detecting an edge vertically extending in the image and a 3 by 3 pixel operator (FIG. 10(b)) for detecting an edge laterally extending in the image, and designating the value, which is determined by summing the calculated results in the respective operators and dividing the sum by 2, as a new density value, or involves designating the square root of the sum of squares of the calculated results in the respective operators as a new density value. FIG. 6(d) illustrates a density profile of the image to which the Sobel filter 213 has been applied. As illustrated in this Figure, the Sobel filter 213 as applied makes the dark defect D2 and an outer edge E2 of the printed mater P prominent, thereby allowing them to be securely detected by the binarization process 214, which will be later described. This embodiment has been described by taking for example a case where the Sobel filter is applied as the edge detection filter. The present invention is not limited to this example. It is possible to apply various filters such as Prewitt or Kirsch filter, provided that they are capable of detecting an edge at which a sharp increase or decrease in density difference occurs.

Then, as illustrated in FIG. 4, the image, to which the Sobel filter 213 has been applied, is subjected to the binarization process 214 that converts the image into binary data according to a predetermined threshold value by the control unit. Whereby, the dark defect D2 and the outer edge E2 are detected. Hereinafter, pixels detected by the binarization process will be referred to detected pixels. Then, the detected pixels are subjected to a masking process 215 by the control unit so as to remove the outer edge E2 from the detected pixels, thereby extracting only the dark defect D2. In this masking process 215, the contour of the printed matter P, which has been extracted by an inspection region extraction process 216, is utilized as a mask so that only the detected pixels present within the mask are extracted. In the inspection region extraction process 216, the inspection image, to which the aforesaid positioning process 209 has been applied, is converted into binary data according to a predetermined threshold value, thereby detecting the contour of the printed matter P. Then, a binary dilation/binary erosion process is applied in order to restore a broken part of the detected contour, perform the size adjustment enabling adaptation to a subtle positional displacement of the outer edge E2 caused by the Sobel filter 213. Thus, a mask to be supplied for masking process 215 is extracted.

Then, the control unit performs a judgment process 217 on the basis of the position, size and the like of thus extracted dark defect D2, which positions, size and the like being respectively compared with predetermined reference values, so as to make a final judgment as to the quality of each printed matter P. The result of the judgment may be informed by means of an alarm, an LED or other light emitting means. It is also possible to provide a mechanism for discharging the printed matter P, which has been judged as a defective printed matter, from the conveyor C.

The dark defect detection process as described above will be effective also for the printed matter having a high degree of density unevenness due to its warping or the like.

FIG. 8 respectively illustrate explanatory views for stepwisely explaining an inspection process of a dark defect in the printed matter P having a high degree of density unevenness. Specifically, the solid line L1 in FIG. 8(a) represents a density profile of the inspection image taken along the line A-A in FIG. 2 and the broken line L2 represents a density profile of the reference image stored in the reference image memory 204, taken along the line B-B in FIG. 2.

Figure 8A:
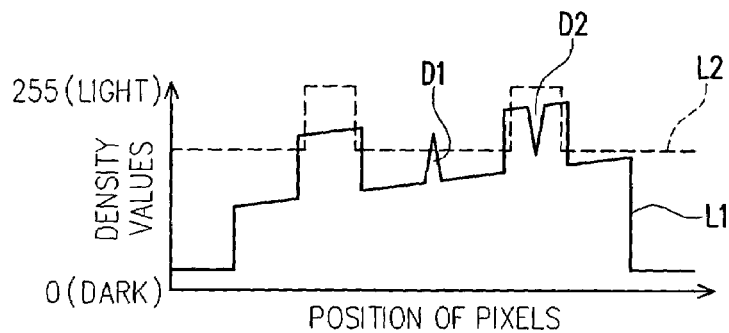
FIG. 8a-8d respectively illustrate explanatory views for stepwisely explaining an inspection process for dark defects in a warped printed matter.
Figure 8B:
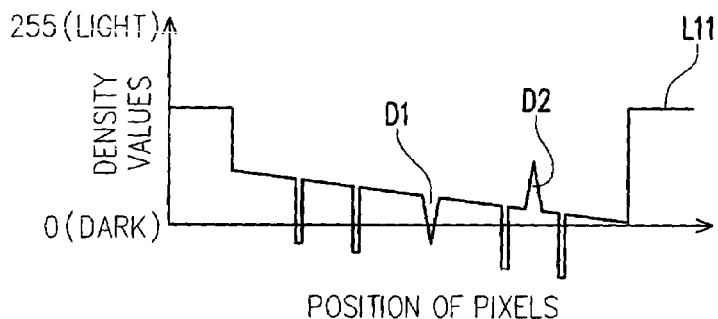
Figure 8C:
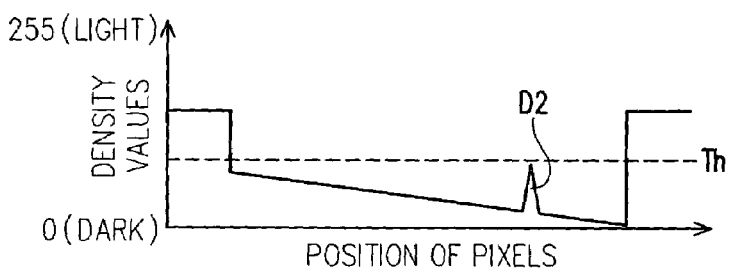
Figure 8D:
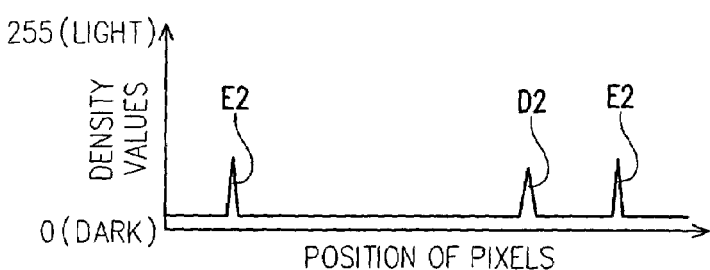

As described above, a differential image having a density profile L11 as illustrated in FIG. 8(b) can be prepared by applying the differencing process 210, or subtracting the solid line L1 from the broken line L2 in FIG. 8(a). Also, an image having a density profile as illustrated in FIG. 8(c) can be produced by applying the density compensation process 212. Herein, assuming that the detection of a defect is made by simply applying the binarization process to an image having the density profile as illustrated in FIG. 8(c), it may pose a problem of impossibility to detect the dark defect D2 according to a threshold Th intended to prevent error detection, through which a non-defect region is detected as a defect region. However, the dark defect detection process in this embodiment, which has the Sobel filter 213 applied prior to the application of the binarization process 214, can reduce the influence of uneven density due to the positional displacement or warping of the printed matter P, and hence performing the binarization process in a stabilized condition. In other words, the Sobel filter 213 is remarkably effective because it enables a secured inspection even for the printed matter P having a high degree of density unevenness. FIG. 8(d) illustrates a density profile of an image to which the Sobel filter 213 has been applied. As illustrated in this Figure, the Sobel filter 213 as applied makes the dark defect D2 and the outer edge E2 of the printed matter P prominent, thereby allowing them to be securely detected by the binarization process 214.

(2) Operation for Detection of Light Defects

Now, the description will be made for the operation for detection of light defects. In this operation, the same processes as those for the operation for detection of dark defects are applied, except that an inspection image, to which the positioning process 209 has been applied, is subjected to the differencing process 211 by the control unit with respect to the reference image stored in the reference image memory 207.

FIG. 9 respectively illustrate explanatory views for stepwisely explaining an inspection operation for light defects of the printed matter P having a high degree of density unevenness. Specifically, the solid line L1 in FIG. 9(a) represents a density profile of the inspection image taken along the line A-A in FIG. 2 and the broken line L2 represents a density profile of the reference image stored in the reference image memory 207, taken along the line B-B in FIG. 3. That is, the broken line L2 represents a density profile as a result of applying the aforesaid gray scale dilation filter 205 and then the density subtraction process 206 ("H" represents a subtracted density value) to a captured image having the density profile as illustrated in FIG. 5(c).

Figure 9A:
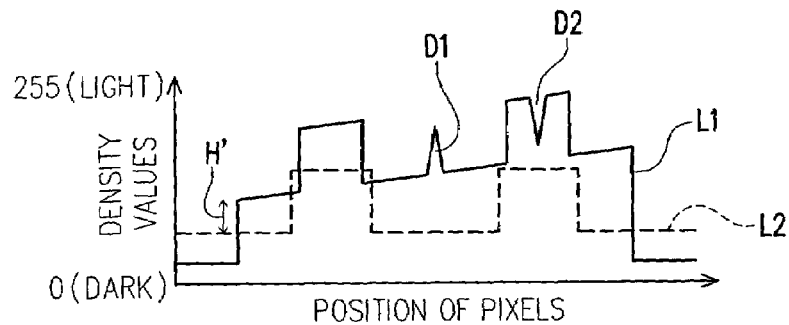
Figure 9B:
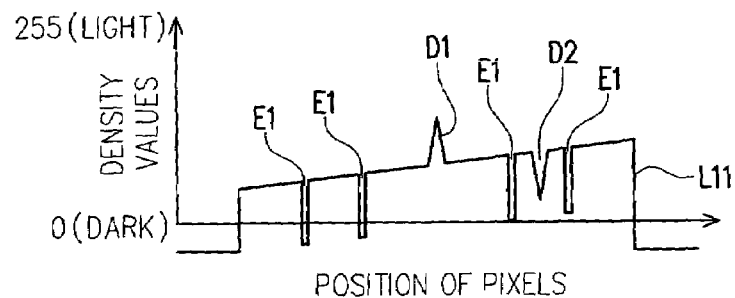

In the differencing process 211, a differential image is prepared by subtracting the reference image stored in the reference image memory 207 from the inspection image to which the positioning process 209 has been applied. That is, a differential image having the density profile L11 as illustrated in FIG. 9(b) is prepared by applying the differencing process 211 or subtracting the broken line L2 from the solid line L1 in FIG. 9(a).

Figure 9C:
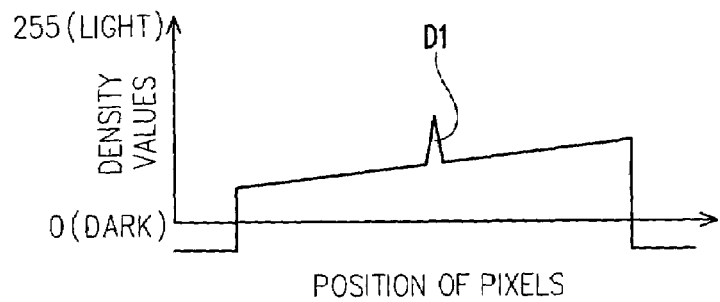

Then, as illustrated in FIG. 4, the differential image prepared by the differencing process 211 is subjected to a density compensation process 218 (the same process as the density compensation process 212) by the control unit. FIG. 9(c) illustrates a density profile of an image to which this density compensation process 218 has been applied. In FIG. 9(c), not only the edge E1 but also the dark defect D2 are illustrated as regions having a negative property, which have been density compensated. In this regard, it is to be noted that the density of the dark defect D12 may not be completely compensated, which depends on the size of the dark defect D2. However, such incomplete compensation of the density of the dark defect D2, which makes the dark defect D2 to be detected by a binarization process 220 (later described), may not pose a problem in a case in which it is enough to only recognize the presence of a defect. However, when it is necessary to identify whether a defect is the light defect D1 or the dark defect D2, the dark defect D2 must be density compensated. Accordingly, the number of times the gray scale erosion filter is applied in the density compensation process 218 is determined by taking into account the size of a possible dark defect as well.

Figure 9D:
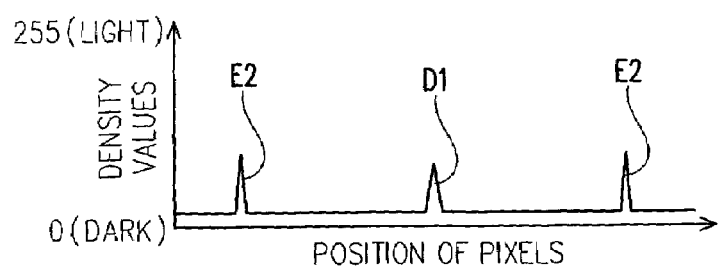

Then, as illustrated in FIG. 4, the image, to which the density compensation process 218 has been applied, is subjected to a Sobel filter 219 (the same filter as the Sobel filter 213) as an edge detection filter by the control unit. FIG. 9(d) illustrates a density profile of an image to which this Sobel filter 219 has been applied. As illustrated in FIG. 9(d), the Sobel filter 219 as applied makes the light defect D1 and the outer edge E2 of the printed mater P prominent, thereby allowing them to be securely detected by the binarization process 220. Likewise to the operation for detection of dark defects, this embodiment has been described by taking for example a case where the Sobel filter is applied as the edge detection filter. The present invention is not limited to this example. It is possible to apply various filters, provided that they are capable of detecting an edge at which a sharp increase or decrease in density difference occurs.

Then, as illustrated in FIG. 4, the image, to which the Sobel filter 219 has been applied, is subjected to the binarization process 220 that converts the image into binary data according to a predetermined threshold value, by the control unit. Whereby, the light defect D1 and the outer edge E2 are detected. Hereinafter, pixels detected by the binarization process will be referred to detected pixels. Then, the detected pixels are subjected to a masking process 221 by the control unit so as to remove the outer edge E2 from the detected pixels, thereby extracting only the light defect D1. In this masking process 221, the contour of the printed matter P, which has been extracted by the inspection region extraction process 216, is utilized as a mask so that only the detected pixels present within the mask are extracted.

Then, the control unit performs a judgment process 222 on the basis of the position, size and the like of thus extracted light defect D1, which position, size and the like being respectively compared with predetermined reference values, so as to make a final judgment as to the quality of each printed matter P. The result of the judgment may be informed by means of an alarm, an LED or other light emitting means. It is also possible to provide a mechanism for discharging the printed matter P, which has been judged as a defective printed matter, from the conveyor C.

As described above, according to the inspection apparatus 100 of this embodiment, it is possible to detect defects of the printed matters with high accuracy by reducing influences of the printed matters which have been displaced from the correct or intended position on the conveyor or warped printed matters. However, in a case where only a light defect or dark defect exists in a specific type of the printed matter P, or performing of only the operation for detection of the dark defect or light defect does not cause a problem, it is possible to apply only either the operation for detection of light defects or the operation for detection of dark defects.

This embodiment has been described by taking for example a case where an area scan CCD camera is employed as an imaging device. The present invention is not limited to this example. It is possible to employ various imaging devices such as a line scan CCD camera, provided they can capture an image of a surface of a printed matter.

Also, this embodiment has been described by taking for example a case where printed matters, which are transferred on the conveyor, are objects to be inspected. The present invention is not limited to this embodiment. That is, the printed matter P, which is not only transferred by the conveyor as described above, but also by any other transferring members can be an object to be inspected. Also, the printed matter, which is in a stationary state during the inspection (e.g., a printed matter which is manually placed within the imaging field of view in a sequential order), can be an object to be inspected. That is, in the present invention, the printed matters under various conditions and states are acceptable as objects to be inspected, as long as they can be positioned within the imaging field of view.

Also, this embodiment has been described by taking for example the case where the gray scale erosion filter, gray scale dilation filter, differencing process, density compensation process and the like are respectively performed according to the image processing program provided in the image processing device. The present invention is not limited to this embodiment. It is possible to perform these processes in a hardware-like manner such as by an exclusively designed electric circuit.

This embodiment has been also described by taking for example the case where a captured image of a non-defect surface of the substrate with printing applied thereon is employed as a reference image when the printed matter as an inspection object is provided by punching or die cutting the substrate. The present invention is not necessarily limited to this embodiment. That is, where printed matters, which are provided not by the punching or die cutting but any other process, are objects to be inspected, a non-defect printed matter among them may be used as a reference image. Even if the printed matters are provided by the punching or die cutting, it is possible to employ a non-defect printed matter among them as a reference image.

Thus, according to the inspection method and inspection apparatus of the present invention, it is possible to achieve the inspection of a defect with high accuracy by reducing influences of a printed matter, which has been displaced from the correct or intended position during the conveyance, or warped printed matter.

This specification is by no means intended to restrict the present invention to the preferred embodiments set forth therein. Various modifications to the inspection method and inspection apparatus, as described herein, may be made by those skilled in the art without departing from the spirit and scope of the present invention as defined in the appended claims.

What is claimed is:

1. A method of inspecting a defect on a surface of a printed matter comprising:
    a step of applying a gray scale erosion filter to a non-defect surface of a printed matter to prepare a gray scale erosion filter applied image and then adding a predetermined density value to said gray scale erosion filter applied image, thereby preparing a reference image;
    a step of subtracting a captured image of the surface of the printed matter to be inspected from said reference image, thereby preparing a differential image; and
    a step of applying a density compensation process to said differential image to prepare a density compensated image, then applying an edge detection filter to said density compensated image to prepare an edge detection filter applied image and then converting said edge detection filter applied image into binary data according to a predetermined threshold value.

2. The method of inspecting the defect on the surface of the printed matter according to claim 1, wherein said density compensation process is achieved by applying a gray scale dilation filter and a gray scale erosion filter, respectively.

3. The method of inspecting the defect on the surface of the printed matter according to claim 1, wherein said density compensation process is achieved by applying a density conversion process.

4. The method of inspecting the defect on the surface of the printed matter according to claim 1, wherein:
    said printed matter is produced by punching or die cutting a substrate, on which printing has been applied; and
    said reference image is prepared on the basis of a captured image of a non-defect surface of the substrate in a state prior to be punched or die cut.

5. A method of inspecting a defect on a surface of a printed matter comprising:
    a step of applying a gray scale dilation filter to a captured image of a non defect surface of a printed matter to prepare a gray scale dilation filter applied image and then subtracting a predetermined density value from said gray scale dilation filter applied image, thereby preparing a reference image;
    a step of subtracting said reference image from a captured image of the surface of the printed matter to be inspected, thereby preparing a differential image; and
    a step of applying a density compensation process to said differential image to prepare a density compensated image, then applying an edge detection filter to said density compensated image to prepare an edge detection filter applied image and then converting said edge detection filter applied image into binary data according to a predetermined threshold value.

6. The method of inspecting the defect on the surface of the printed matter according to claim 5, wherein said density compensation process is achieved by applying a gray scale dilation filter and a gray scale erosion filter, respectively.

7. The method of inspecting the defect on the surface of the printed matter according to claim 5, wherein said density compensation process is achieved by applying a density conversion process.

8. The method of inspecting the defect on the surface of the printed matter according to claim 5, wherein:
    said printed matter is produced by punching or die cutting a material with printing applied thereon; and
    said reference image is prepared on the basis of a captured image of a non-defect surface of the substrate in a state prior to be punched or die cut.

9. An apparatus for inspecting a defect on a surface of a printed matter comprising:
    an imaging device for capturing a surface of a printed matter to prepare a captured image; and
    an image processing device for applying image processing to said captured image of said surface of said printed matter; wherein said image processing device includes:
    a means of applying a gray scale erosion filter to a captured image of a non-defect surface of a printed matter to prepare a gray scale erosion filter applied image;
    a means of preparing a reference image by adding a predetermined density value to said gray scale erosion filter applied image;
    a means of preparing a differential image by subtracting a captured image of a surface of a printed matter to be inspected from said reference image; p1 a means of applying a density compensation process to said differential image to prepare a density compensated image;
    a means of applying an edge detection filter to said density compensated image to prepare an edge detection filter applied image; and
    a means of converting said edge detection filter applied image into binary data according to a predetermined threshold value.

10. An apparatus for inspecting a defect on a surface of a printed matter comprising:
    an imaging device for capturing a surface of a printed matter to prepare a captured image; and
    an image processing device for applying image processing to said captured image of said surface of said printed matter; wherein said image processing device includes:
    a means of applying a gray scale dilation filter to a captured image of a non-defect surface of a printed matter to prepare a gray scale dilation filter applied image;

a means of preparing a reference image by subtracting a predetermined density value from said gray scale dilation filter applied image;

a means of preparing a differential image by subtracting said reference image from a captured image of a surface of a printed matter to be inspected;

a means of applying a density compensation process to said differential image to prepare a density compensated image;

a means of applying an edge detection filter to said density compensated image to prepare an edge detection filter applied image; and a means of converting said edge detection filter applied image into binary data according to a predetermined threshold value.

* * * * *